(12) United States Patent
Ortiz

(10) Patent No.: US 7,815,636 B2
(45) Date of Patent: Oct. 19, 2010

(54) AUTO-SAFETY SHUT-OFF FOR ENERGY BASED DEVICES

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 100 days.

(21) Appl. No.: 11/164,557

(22) Filed: Nov. 29, 2005

(65) Prior Publication Data

US 2007/0123849 A1    May 31, 2007

(51) Int. Cl.
*A61B 18/12* (2006.01)

(52) U.S. Cl. ............... 606/41; 606/42; 606/43; 606/44; 606/45; 606/46; 606/47; 606/48; 606/49; 606/50; 606/51; 606/52

(58) Field of Classification Search ............... 606/41–42
See application file for complete search history.

(56) References Cited

U.S. PATENT DOCUMENTS

| | | | |
|---|---|---|---|
| 5,599,347 A | | 2/1997 | Hart et al. |
| 5,658,279 A | | 8/1997 | Nardella et al. |
| 5,772,660 A | * | 6/1998 | Young et al. ............... 606/42 |
| 5,997,533 A | * | 12/1999 | Kuhns ........................ 606/41 |
| 6,165,175 A | | 12/2000 | Wampler et al. |
| 6,296,640 B1 | | 10/2001 | Wampler et al. |
| 6,511,480 B1 | * | 1/2003 | Tetzlaff et al. ............. 606/51 |
| 6,623,437 B2 | * | 9/2003 | Hinchliffe et al. .......... 600/564 |
| 2002/0141204 A1 | * | 10/2002 | Gao .......................... 362/570 |
| 2004/0028459 A1 | * | 2/2004 | Wetzel et al. .............. 401/194 |
| 2004/0056949 A1 | * | 3/2004 | Lin ............................ 348/61 |

FOREIGN PATENT DOCUMENTS

DE    4416499    11/1995

* cited by examiner

*Primary Examiner*—Ahmed M Farah
*Assistant Examiner*—Aaron Roane
(74) *Attorney, Agent, or Firm*—Nutter McClennen & Fish LLP

(57) ABSTRACT

Various methods and devices are provided for surgically treating tissue. In one embodiment, the device can include a shaft having proximal and distal ends and a conductive tip disposed within the distal end of the shaft and movable between a first and second position. In the first position, the conductive tip is disconnected from a conductive contact which is adapted to communicate with an energy source. In the second position, the conductive tip is in contact with the conductive contact such that energy can be delivered from an energy source through the conductive contact to the conductive tip. The conductive tip can have a variety of shapes and sizes, but in one exemplary embodiment, the conductive tip is a blunt tip. The conductive contact can include at least one lead extending therefrom and adapted to communicate with an energy source.

7 Claims, 9 Drawing Sheets

AUTO-SAFETY SHUT-OFF FOR ENERGY BASED DEVICES

BACKGROUND OF THE INVENTION

A wide variety of devices are used during surgical procedures for treating tissue, such as for cutting and/or coagulation. Electrosurgical instruments have been developed that utilize energy for performing these functions. For example, instruments utilizing radio frequency (RF) energy provide current and/or heat that can be used for cutting and coagulating tissues. These devices only required small amounts of force to pass through tissue, while only affecting the tissue directly near the portion of the device receiving the energy.

While the use of energy for such devices is increasingly popular, it is not without its disadvantages. Due to the low force of penetration needed to pass through tissue, there is the risk of penetrating additional tissue that is intended to be left unharmed during the procedure. This could result in damage and/or destruction of sections of secondary tissue or organs.

Accordingly, there is a need for improved devices and methods for cutting and/or coagulating tissue that also protects secondary tissue.

BRIEF SUMMARY OF THE INVENTION

The present invention provides devices and methods for surgically treating tissue, such as by cutting and/or coagulating tissue. In one exemplary embodiment, the device can include a shaft having proximal and distal ends and a conductive tip disposed within the distal end of the shaft and movable between a first and a second position. In the first position, the conductive tip is disconnected from a conductive contact which is adapted to communicate with an energy source. In the second position, the conductive tip is in contact with the conductive contact such that energy can be delivered from an energy source through the conductive contact to the conductive tip. The conductive tip can have a variety of shapes and sizes, but in one exemplary embodiment, the conductive tip is a blunt tip. The conductive contact can include at least one lead extending therefrom and adapted to communicate with an energy source.

In one exemplary embodiment, the device can further include a conductive connector coupled to and extending proximally from the conductive tip. The conductive connector can be adapted to communicate with the conductive contact such that energy can be delivered from the conductive contact, through the conductive connector, to the conductive tip when the conductive tip is in the second position. While the conductive connector can have a variety of configurations, in one exemplary embodiment the conductive connector can include a collar disposed around a sheath extending through the shaft, a first extension arm coupled to the collar and extending distally toward the conductive tip, and a second extension arm coupled to the collar and extending proximally toward the conductive contact.

In other exemplary embodiment, the device can further include a biasing element effective to bias the conductive tip to the first position. While the biasing element can have a variety of configurations, in one embodiment, the biasing element comprises a spring.

Another exemplary embodiment of a device for surgically treating tissue, such as by cutting and/or coagulating tissue, includes a conductive tip movably disposed within a housing and biased to an electrically deactivated position. A force applied to the conductive tip is adapted to move the conductive tip to an electrically activated position. In one embodiment, the device can includes an electrical connection assembly adapted to allow for an electrical connection between the conductive tip and an energy source when the conductive tip is in the electrically activated position. The electrical connection assembly can include a conductive contact adapted to couple to an energy source and a conductive connector extending between the conductive tip and the conductive contact such that energy can be delivered from the conductive contact through the conductive connector to the conductive tip when the conductive tip is in the electrically activated position. The electrical connection assembly can further include a biasing element for biasing the conductive tip to the electrically deactivated position. In one embodiment, the conductive connector is slidably disposed around a sheath disposed through the housing. An insulative coating can be disposed around a portion of the conductive tip. The conductive tip can be disposed within a sheath extending through the housing, the sheath being adapted to insulate the conductive tip from the housing.

Also disclosed herein are methods for surgically treating tissue, such as by cutting and/or coagulating a tissue. In one embodiment, the method can include contacting tissue with a conductive tip of an electrosurgical device such that the tissue causes the conductive tip to move to an electrically activated position whereby electrical energy is delivered to the conductive tip to treat the tissue. The conductive tip moves to an electrically deactivated position after it passes through the tissue, or otherwise loses contact with the tissue. For example, in one embodiment, the pressure of the tissue on the conductive tip can overcome a biasing force applied to the conductive tip to move the conductive tip to the electrically activated position. The biasing force can be effective to move the conductive tip to the electrically deactivated position after it passes through or loses contact with the tissue.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for cutting and/or coagulating tissue. In particular, methods and devices are provided which can include an auto-shutoff feature which terminates the energy supply to the device to prevent penetration and/or damage to secondary tissue intended to be left unharmed during a procedure.

Figure 1A:
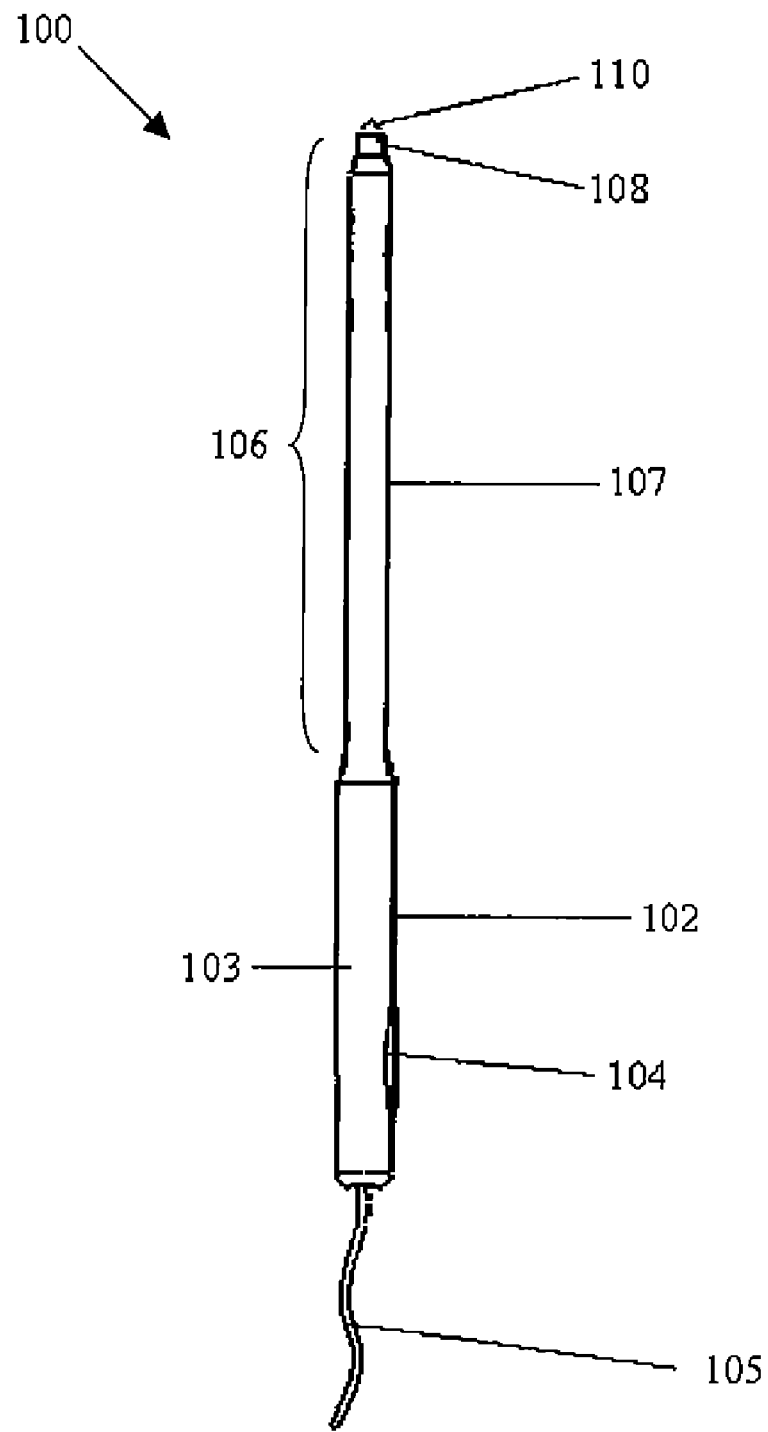
FIG. 1A is a side view of an exemplary embodiment of a tissue cutting and/or coagulation device.
Figure 1B:
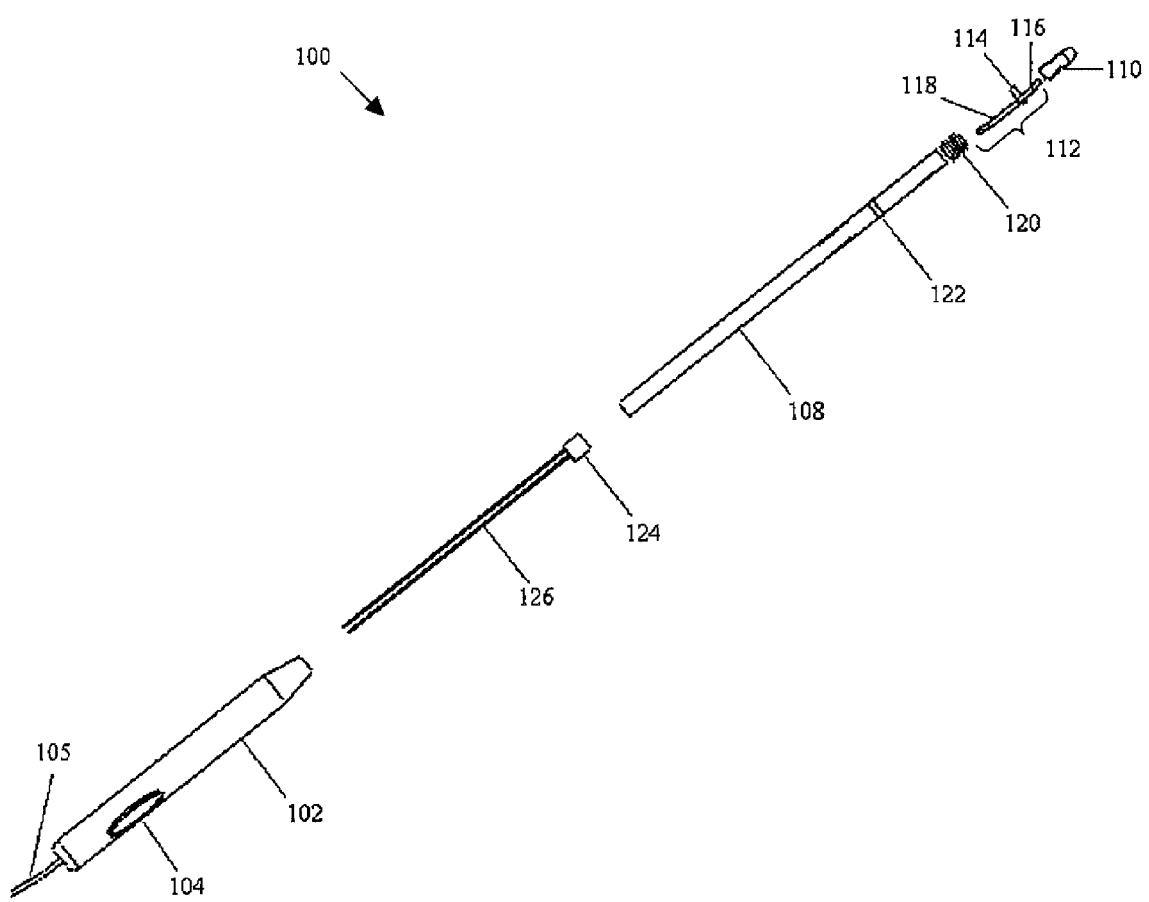
FIG. 1B is an exploded view of the device shown in FIG. 1A.

FIGS. 1A-1B illustrate an exemplary embodiment of a device having an auto shut-off feature. As shown, device 100 can include a housing 102 with a distal tip 106 extending therefrom. The distal tip 106 includes a shaft 107 with a conductive tip 110, which is movable between an activated and a deactivated position, formed at a distal end thereof. As shown in FIG. 1B, an electrical connection assembly is disposed within the shaft 107, and can include a sheath 108, a conductive contact 124 with leads 126, and a conductive connector 112 that extends from the conductive tip 110 to the conductive contact 124. Proximal movement of the conductive tip 110 places the conductive connector 112 into electrical communication with the conductive contact 124 to establish an electrical connection between the conductive tip 110 and the conductive contact 124 to activate the conductive tip 110. The electrical connection assembly can also include a biasing element to bias the conductive tip 110, for example, to a distal, deactivated position. A person skilled in the art will appreciate that the biasing element can alternatively be configured to bias the conductive tip 110 to an activated position.

One skilled in the art will appreciate that the conductive tip 110 is a tissue-affecting element that is adapted to treat tissue in a variety of ways. For example, the conductive tip 110 can penetrate tissue, such as by cutting, or it can coagulate tissue. When the conductive tip 110 is adapted to penetrate tissue, it can be blunt, such that tissue penetration can be effected or assisted by electrical energy, or it can be sharpened so that it penetrates tissue by mechanical action.

The housing 102 can have a variety of configurations to promote ergonomics and ease of use. As shown in FIGS. 1A-1B, the housing 102 includes a proximal end having a handle 103 to allow a user to hold the device 100 during use. The housing 102 can also include an actuating element 104 to enable the delivery of energy from an energy source. By way of non-limiting example, the actuating element 104 can include a button, a switch, a knob, or any other configuration to allow for the control of energy from an energy source. In lieu of an actuating element disposed on the handle 103, one skilled in the art will appreciate that the actuating element can be located elsewhere, including on a foot pedal. The handle 103 is also adapted to be coupled to an energy source. For example, power cord 105, as shown in FIGS. 1A-1B, can couple to the handle 103 at a first end and connect to a power outlet at a second end.

Figure 2:
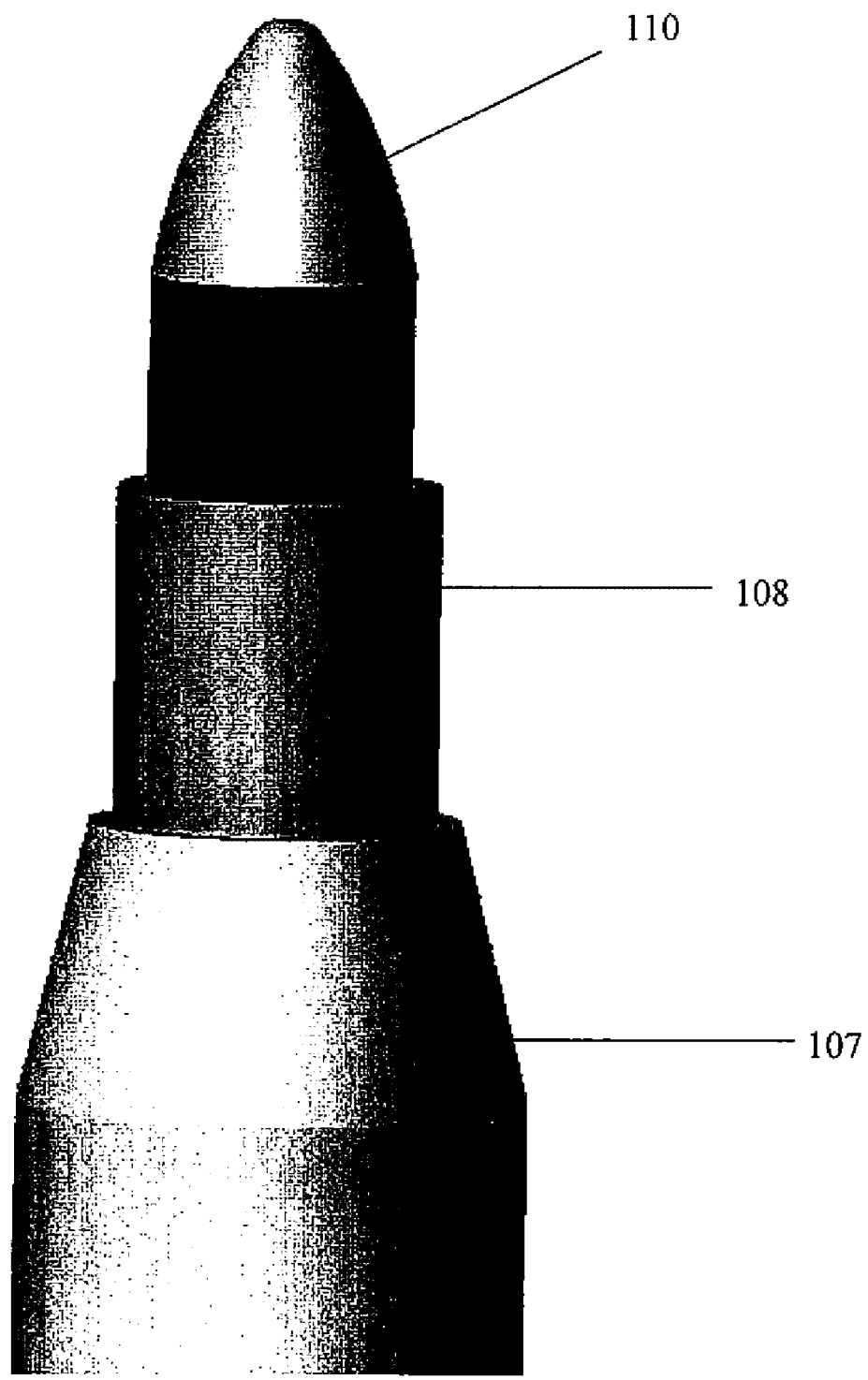
FIG. 2 is a perspective view of an exemplary embodiment of the distal end of a tissue cutting and/or coagulation device showing different coatings applied to the distal end.

The conductive tip 110 can have various shapes and sizes as well. In one embodiment, illustrated in FIG. 2, the conductive tip 110 generally has a bullet-shaped configuration. The distal end of the conductive tip 110 has a blunt shape which is adapted to contact and treat a tissue, and the proximal end includes a contact surface to establish an electrical connection with the conductive connector 112. In one exemplary embodiment, the conductive tip 110 is configured to maintain the conductive tip 110 within the sheath 108. For example, the conductive tip 110 can include a flange (not shown) adapted to couple to the sheath 108, or the conductive tip 110 can be attached to the conductive connector 112.

The conductive tip 110 can be made from and/or coated with a variety of materials. While the conductive tip 110 is adapted to be conductive, the conductive tip 110 need not be made entirely of conductive material as long as a conductive path exists through the conductive tip 110. For example, if made from entirely conductive materials, the conductive tip 110 can be coated with an insulating material. Additionally, the conductive tip 110 can be made from a composite material, which includes conductive and non-conductive materials. Exemplary materials include insert molded stainless steels with a plastic or elastomeric overcoating, or steel or titanium with a non conductive teflon spray coating.

As noted above, the conductive tip 110 is moveable between a deactivated and activated position. In its activated position, the conductive tip 110 is in contact with the conductive contact 124 to allow energy delivery from an energy source through the conductive contact 124 to the conductive tip. The force of the blunt distal end of the conductive tip 110 against a tissue to be treated causes the conductive tip 110 to move inwardly, in a proximal direction, within the sheath 108. When so positioned, the contact surface disposed on the proximal end of the conductive tip 110 pushes the conductive connector 112 into contact with the conductive contact 124, causing an electrical connection between the conductive tip 110 and the conductive contact 124 through the conductive connector 112 to be formed. Energy can be delivered from the energy source through the conductive contact 124 to the conductive tip 110 to allow conductive tip 110 to heat up and cut and/or coagulate the tissue. After the conductive tip 110 has penetrated the target tissue, or the conductive tip 110 has been moved out of contact with the target tissue, the pressure is removed from the conductive tip 110, thereby allowing the conductive tip 110 to move distally to break the electrical connection to the conductive contact 124 and cease the delivery of energy to the conductive tip 110. The conductive tip 110 can cool quickly to prevent penetration or damage to secondary tissue intended to be left unharmed.

The electrical connection assembly provides an electrical connection between the conductive tip 110 and the conductive contact 124, and can be in any configuration to establish such an electrical connection. In an exemplary embodiment, the electrical connection assembly includes a sheath 108, a conductive contact 124 disposed around and attached to the proximal end of the sheath 108, and a conductive connector 112 extending between the conductive tip 110 and the conductive contact 124, as shown in FIG. 3A.

Figure 3A:
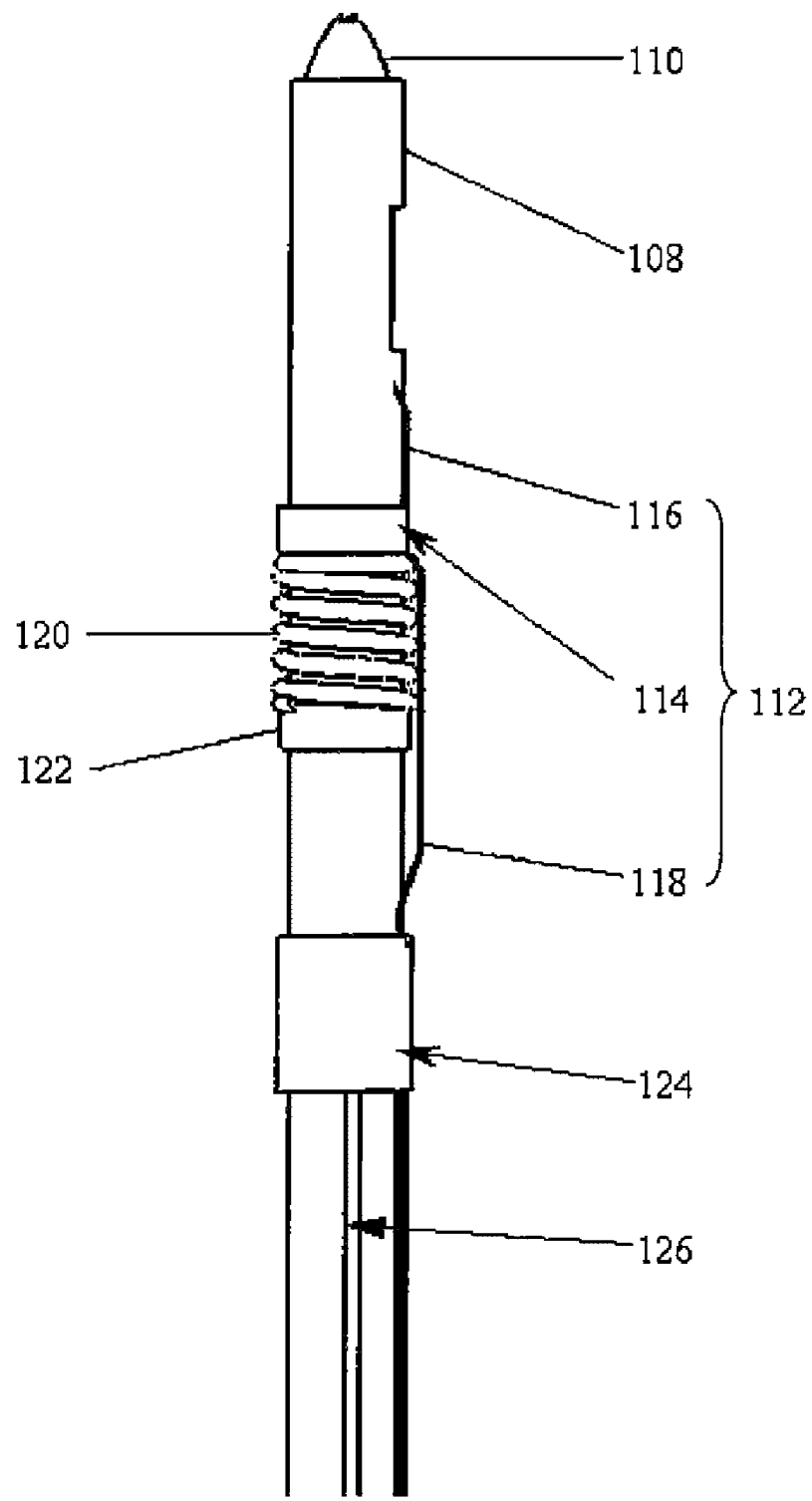
FIG. 3A is side view of an exemplary embodiment of a distal tip of the device shown in FIGS. 1A-1B.
Figure 3B:
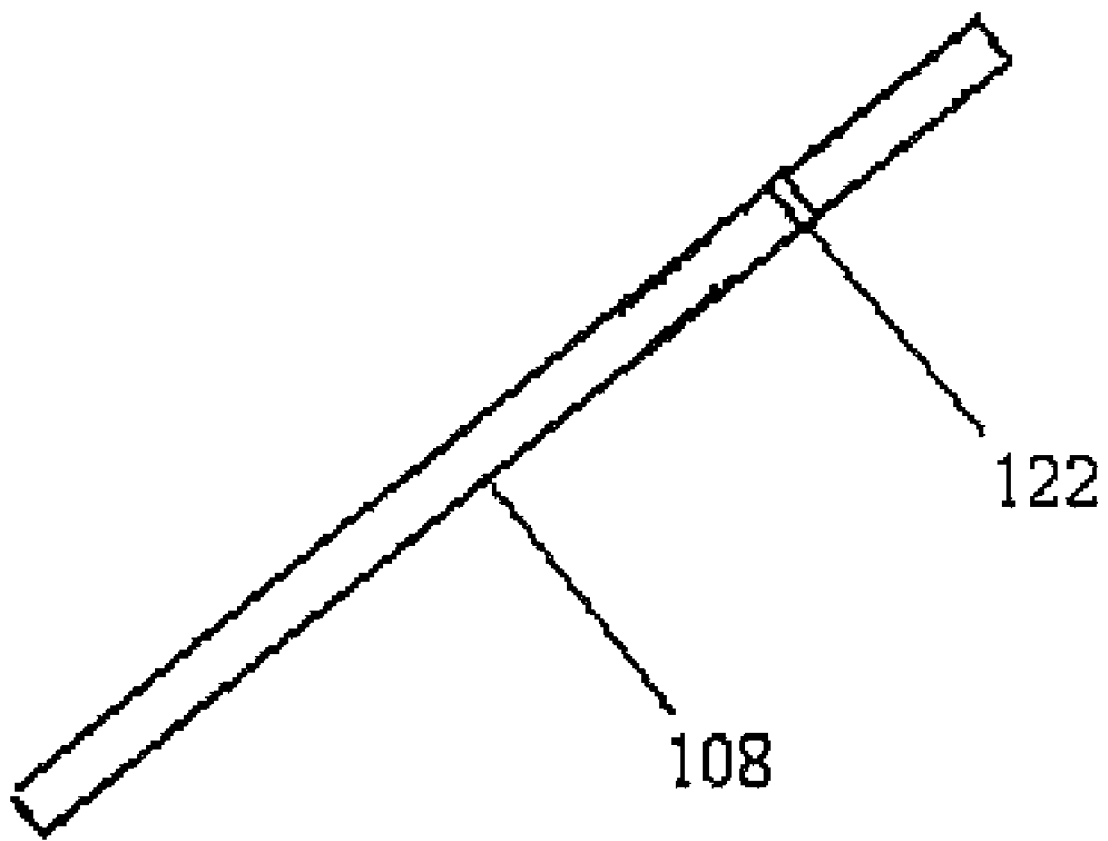
FIG. 3B is a side view of an exemplary embodiment of a sheath of the device shown in FIG. 3A.

The sheath 108, as shown in FIG. 3B, is generally an elongated, hollow cylinder disposed in the shaft 107 (as also shown in FIG. 1A). The sheath 108 can support the conductive structures of the electrical connection assembly, as well as support the distal end of the conductive tip 110 which is disposed within the sheath 108. The sheath 108 can be made of an insulating material such that it is adapted to insulate the conductive tip 110 from the shaft 107. In one exemplary embodiment, the sheath 108 includes a flange 122, which acts as a spring stop for a biasing element, as discussed below.

The conductive contact 124 shown in FIG. 3A is disposed around the proximal end of the sheath 108 and fixed thereto. One or more leads 126 extend from the conductive contact 124 through the housing 102 (shown in FIGS. 1A-1B) and are adapted to communicate with an energy source to provide energy to the conductive tip 110 when it is in the activated position.

Figure 3C:
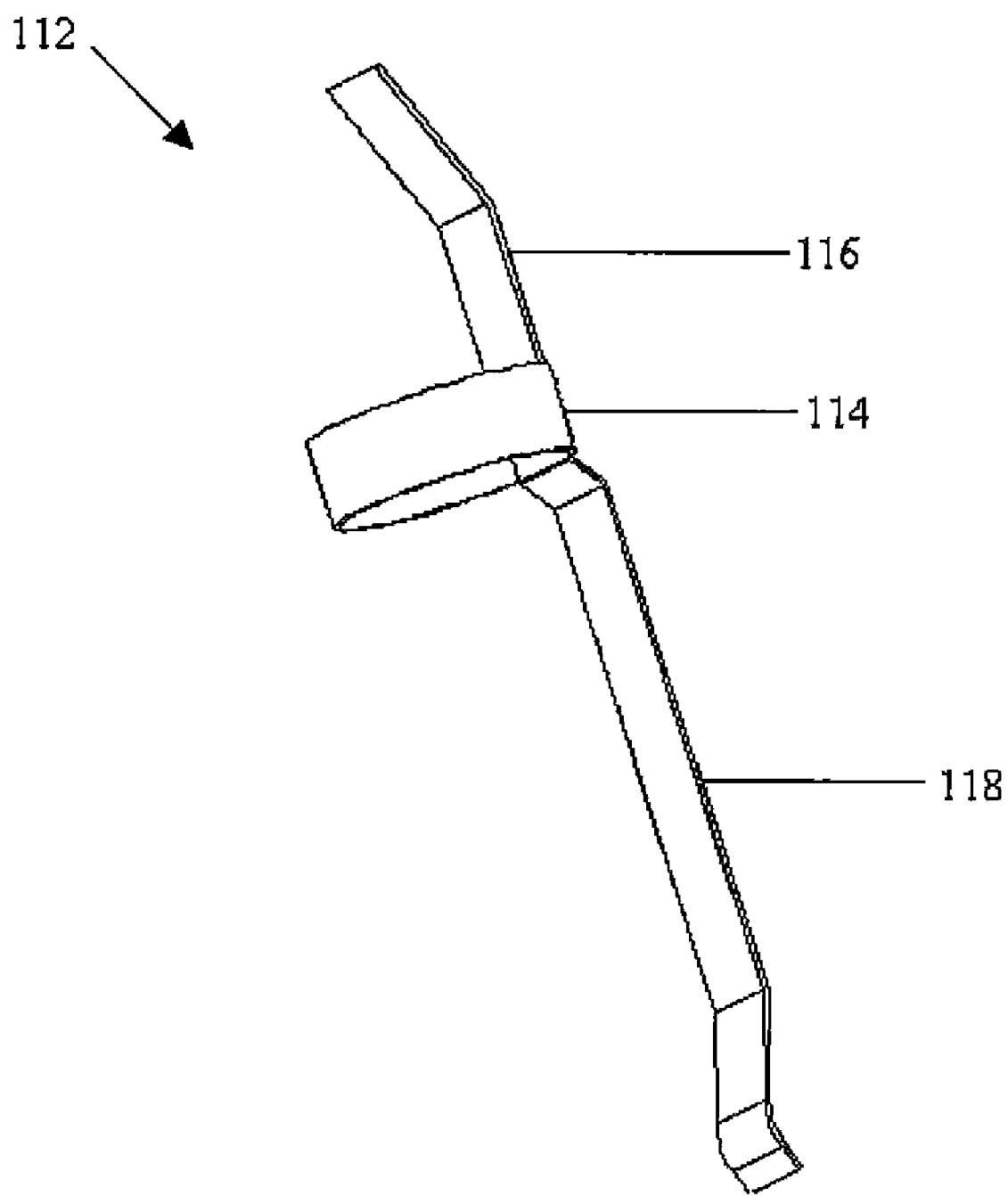
FIG. 3C is a perspective view of an exemplary embodiment of a conductive connector of the device shown in FIG. 3A.

The conductive connector 112 extends between the conductive tip 110 and the conductive contact 124 and is adapted to communicate with the conductive contact 124 to deliver energy from the conductive contact 124, through the conductive connector 112, to the conductive tip 110 when the conductive tip 110 is in an activated position. As shown in FIG. 3C, in one exemplary embodiment, the conductive connector 112 includes a collar 114 slidably disposed around the sheath 108 and abutting a distal end of a biasing element (as shown in FIG. 3A). A first extension arm 116 extends distally from the collar 114 and a second extension arm 118 extends proximally from the collar 114. The first extension arm 116 extends distally from the collar 114 towards the contact surface disposed on the proximal end of the conductive tip 110 and abuts the conductive tip 110 allowing for electrical communication between the conductive tip 110 and the conductive connector 112. The second extension arm 118 extends proximally from the collar 114 towards the conductive contact 124. The conductive contact 124 is in electrical communication with the conductive connector 112 when the conductive tip 110 is in an activated position and depressed into the sheath 108. The conductive tip 110 pushes the conductive connector 112 proximally, causing the conductive connector 112 to slide along the sheath 108 and into contact with the conductive contact 124. While the exemplary embodiment has the conductive connector 112 in constant contact with the conductive tip 110 and in contact with the conductive contact 124 only in the activated position, one skilled in the art will appreciate that any combination of contact between the conductive connector 112 and the conductive tip 110 and the conductive contact 124 would be acceptable, as long as there is not an electrical connection between the conductive tip 110 and the conductive contact 124 while the conductive tip 110 is in the deactivated position.

As noted above, in an exemplary embodiment of the invention, the electrical connection assembly includes a biasing element to bias the conductive tip 110 to an activated position or, alternatively, a deactivated position. By way of one example, the biasing element can be a spring 120, as shown in FIG. 3A, for biasing the conductive tip 110 to a deactivated position. The spring 120 is disposed around the sheath 108 with its proximal end resting against the flange 122. The biasing force of the spring 120 on the conductive tip 110 can be overcome by the pressure of a tissue on the conductive tip 110, allowing the conductive tip 110 to be depressed into the activated position when it is in contact with a tissue. This causes the spring 120 to compress, allowing the conductive connector 112 to slide along the sheath 108 and into contact with conductive contact 124. A person skilled in the art will appreciate that a variety of other devices, or configurations, suitable for biasing can be used as the biasing element.

Figure 4A:
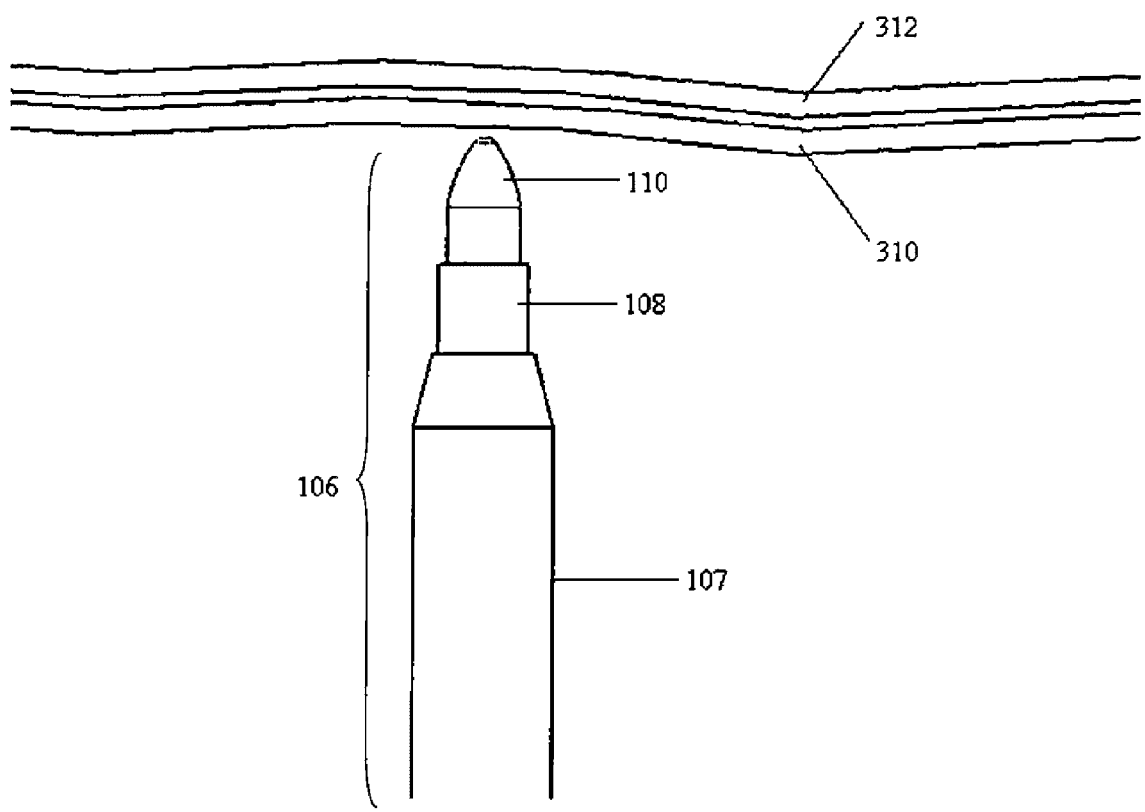
FIG. 4A is a side view of a tissue cutting and/or coagulation device prior to contact with a target tissue.
Figure 4B:
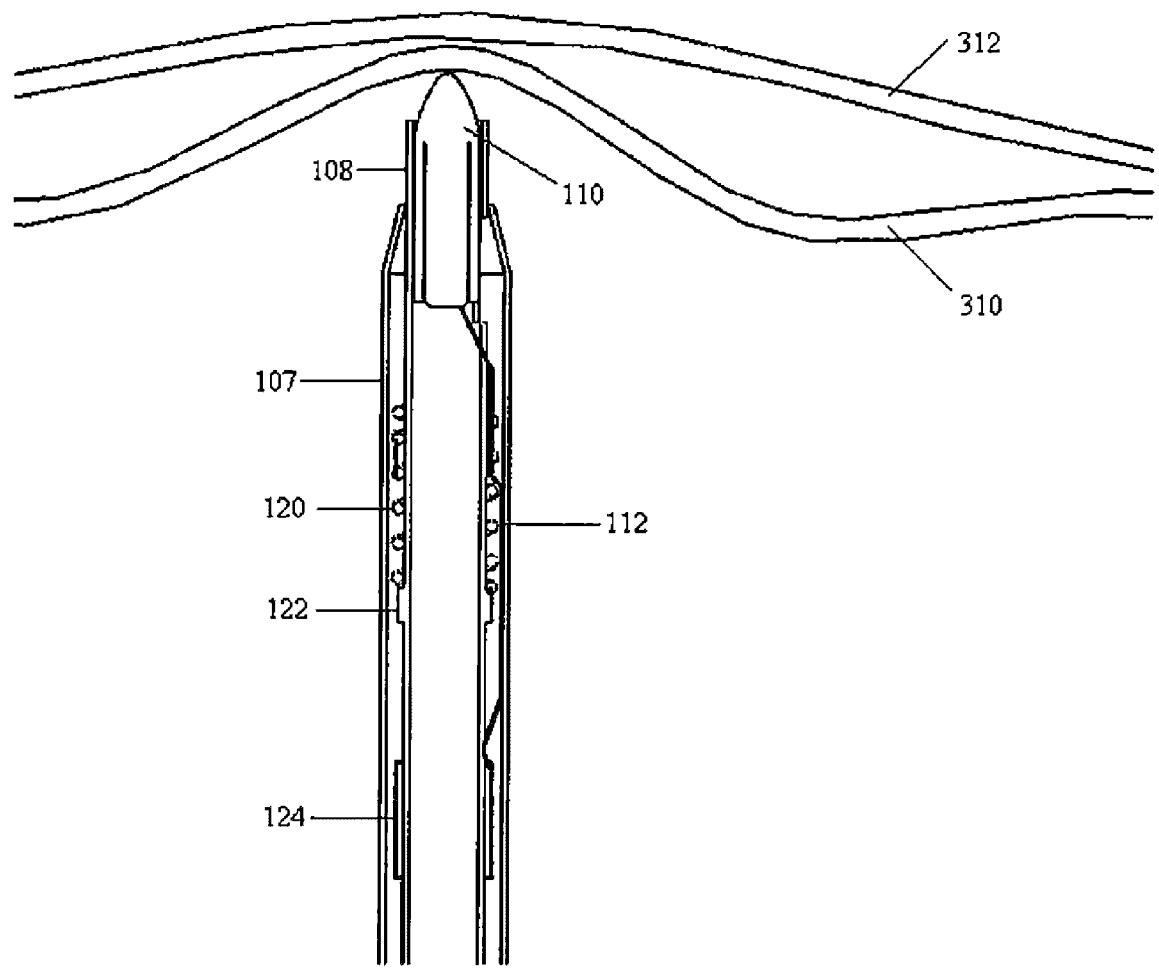
FIG. 4B is a side view of a tissue cutting and/or coagulation device during the cutting and/or coagulation of a target tissue.
Figure 4C:
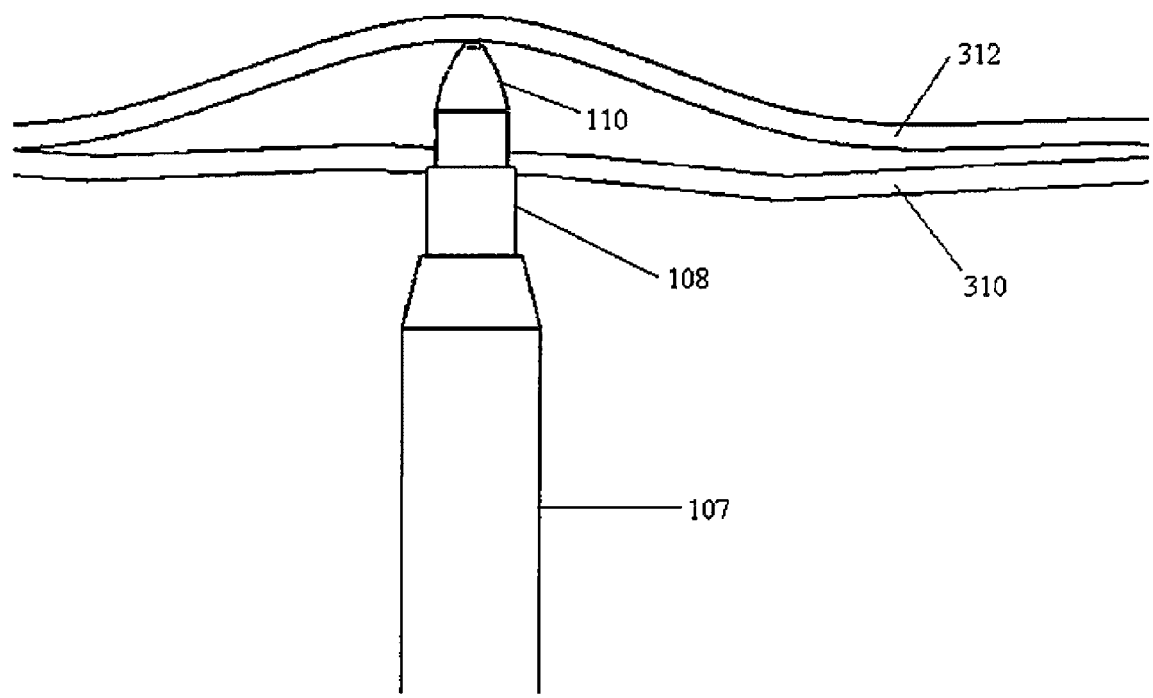
FIG. 4C is a side view of a tissue cutting and/or coagulation device after the device has cut through the target tissue.

As previously explained, the present invention generally provides methods for treating tissue, such as by cutting and/or coagulating tissues using an auto shut-off device. FIGS. 4A-4C illustrate an exemplary method for cutting and/or coagulating tissue using a device of the present invention. FIG. 4A shows an illustrative embodiment of a distal end of a device 100 prior to contact with a tissue 310 to be cut and/or coagulated. The conductive tip 110 is in a deactivated position because it is biased distally to the deactivated position. Since there is no electrical connection between the conductive tip 110 and the conductive contact 124, the conductive tip 110 is not able to deliver electrical energy and/or heat to the tissue 310 and it is unable to affect any tissue.

FIG. 4B shows a cross-sectional view of the distal end of the device in contact with tissue 310. The pressure acting on the conductive tip 110, as a result of the contact between the tissue 310 and the conductive tip 110, is sufficient to overcome the biasing force on the conductive tip 110. This allows the conductive tip 110 to move proximally, causing the conductive connector 112 to move slidably along the sheath 108 and into electrical communication with the conductive contact 124. More specifically, when so depressed, the spring 120 is compressed, allowing the conductive connector 112 to slide proximally along the sheath 108 and into contact with conductive contact 124, causing an electrical connection between the conductive tip 110 and the conductive contact 124 through the conductive connection 112. After the conductive tip 110 has passed through the tissue 310, as shown in FIG. 4C, the pressure from the tissue 310 is removed, and the conductive tip rebounds to a deactivated position. The energy supply to the conductive tip 110 is thus shut off, preventing penetration of a secondary tissue 312 intended to be left unharmed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A tissue affecting surgical device, comprising: a shaft having proximal and distal ends and extending from a handle housing; a tissue affecting electrically conductive tip disposed within the distal end of the shaft; and an elongate electrically conductive connector having a distally extending arm in contact with the conductive tip and a proximally extending arm configured to contact an electrically conductive contact; wherein movement of the conductive tip and the conductive connector longitudinally along the shaft to a first position causes the proximally extending arm on the conductive connector to disconnect from an electrically conductive contact adapted to communicate with an electrical energy source, and movement of the conductive tip and the conductive connector longitudinally along the shaft to a second position causes the proximally extending arm on the conductive connector to contact the conductive contact such that energy can be delivered from the energy source through the conductive contact to the conductive tip, wherein the conductive tip has a blunt distal end.

2. The device of claim 1, wherein the conductive connector includes a collar disposed around a sheath extending through the shaft, the distally extending arm being coupled to the collar and extending distally toward the conductive tip, and the proximally extending arm being coupled to the collar and extending proximally toward the conductive contact.

3. The device of claim 2, wherein the conductive connector extends along an outer surface of the sheath.

4. The device of claim 1, further comprising a biasing element effective to bias the conductive tip to the first position.

5. The device of claim 4, wherein the biasing element comprises a spring.

6. The device of claim 1, wherein the conductive contact includes at least one lead extending therefrom and adapted to communicate with an electrical energy source.

7. The device of claim 1, wherein the conductive tip is bullet-shaped.

* * * * *